United States Patent
Danielsson et al.

(10) Patent No.: US 9,867,580 B2
(45) Date of Patent: Jan. 16, 2018

(54) X-RAY IMAGING BASED ON IMAGE DATA FROM A PHOTON-COUNTING MULTI-BIN X-RAY DETECTOR

(71) Applicant: PRISMATIC SENSORS AB, Stockholm (SE)

(72) Inventors: Mats Danielsson, Taby (SE); Hans Bornefalk, Uppsala (SE); Xuejin Liu, Taby (SE); Ben Huber, Stockholm (SE); Han Chen, Stockholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 0 days.

(21) Appl. No.: 15/504,159

(22) PCT Filed: Nov. 10, 2014

(86) PCT No.: PCT/SE2014/051330
§ 371 (c)(1),
(2) Date: Feb. 15, 2017

(87) PCT Pub. No.: WO2016/076767
PCT Pub. Date: May 19, 2016

(65) Prior Publication Data
US 2017/0273640 A1    Sep. 28, 2017

(51) Int. Cl.
*A61B 6/00*    (2006.01)
*A61B 6/03*    (2006.01)
(Continued)

(52) U.S. Cl.
CPC .............. *A61B 6/03* (2013.01); *A61B 6/4241* (2013.01); *A61B 6/482* (2013.01); *A61B 6/5205* (2013.01);
(Continued)

(58) Field of Classification Search
CPC ........ A61B 6/4241; A61B 6/482; A61B 6/585
See application file for complete search history.

(56) References Cited

U.S. PATENT DOCUMENTS

2009/0039273 A1   2/2009   Tkaczyk et al.
2010/0215230 A1   8/2010   Bornefalk et al.
(Continued)

FOREIGN PATENT DOCUMENTS

WO   2013/005848 A1   1/2013
WO   2014/098196 A1   6/2014

OTHER PUBLICATIONS

Yveborg, M. et al., "Task Based Weights for Spectral Computed Tomography," Proc. of SPIE, vol. 8313, pp. 831334-1-831334-6, downloaded Aug. 2015.
(Continued)

*Primary Examiner* — Dani Fox
(74) *Attorney, Agent, or Firm* — Young & Thompson

(57) ABSTRACT

There is provided a method and corresponding system and apparatus for image reconstruction based on image data from a photon-counting multi-bin x-ray detector. The method includes determining (S1) parameter(s) of a given functional form of the relationship between comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum. The method also includes performing (S2) image reconstruction based on the image data and the determined parameter(s). In this way, efficient high-quality image reconstruction can be achieved.

17 Claims, 14 Drawing Sheets

(51) Int. Cl.

| | |
|---|---|
| G01N 23/04 | (2006.01) |
| G01T 1/17 | (2006.01) |
| G01T 1/24 | (2006.01) |
| G01T 7/00 | (2006.01) |
| G06T 11/00 | (2006.01) |

(52) U.S. Cl.
CPC ............. *A61B 6/583* (2013.01); *A61B 6/585* (2013.01); *G01N 23/04* (2013.01); *G01T 1/17* (2013.01); *G01T 1/24* (2013.01); *G01T 7/005* (2013.01); *G06T 11/003* (2013.01); *G06T 11/005* (2013.01)

(56) References Cited

U.S. PATENT DOCUMENTS

| | | |
|---|---|---|
| 2013/0148873 A1 | 6/2013 | Arenson et al. |
| 2013/0182818 A1 | 7/2013 | Miyazaki |
| 2014/0233694 A1 | 8/2014 | Wang et al. |
| 2014/0254749 A1 | 9/2014 | Steadman Booker et al. |
| 2014/0328464 A1 | 11/2014 | Proksa |
| 2014/0328466 A1 | 11/2014 | Proksa et al. |

OTHER PUBLICATIONS

Taguchi, K. et al., "Vision 20/20: Single Photon Counting X-Ray Detectors in Medical Imaging," Medical Physics, vol. 40, No. 10, 100901-1-100901-19, Oct. 2013.

Taguchi, K. et al., "Modeling the Performance of a Photon Counting X-Ray Detector for CT: Energy Response and Pulse Pileup Effects," Med. Phys., vol. 32, No. 2, pp. 1089-1102, Feb. 2011.

Schirra, C. et al., "Statistical Reconstruction of Material Decomposed Data in Spectral CT," IEEE Transactions on Medical Imaging, vol. 32, No. 7, pp. 1249-1257, Jul. 2013.

Roessl, E. et al., "Sensitivity of Photon-Counting Based K-Edge Imaging in X-Ray Computed Tomography," IEEE Transactions on Medical Imaging, vol. 30, No. 9, pp. 1678-1690, Sep. 2011.

Roessl, E. et al., "K-Edge Imaging in X-Ray Computed Tomography Using Multi-Bin Photon Counting Detectors," Phys. Med. Biol., vol. 52, pp. 4679-4696, 2007.

Persson, M. et al., "Energy-Resolved CT Imaging with a Photon-Counting Silicon-Strip Detector," Phys. Med. Biol., vol. 59, pp. 6709-6727, 2014.

Persson, M. et al., "A Framework for Evaluating Threshold Variation Compensation Methods in Photon Counting Spectral CT," IEEE Transactions on Medical Imaging, vol. 31, No. 10, pp. 1861-1874, Oct. 2012.

Liu, X. et al., "A Silicon-Strip Detector for Photon-Counting Spectral CT: Energy Resolution From 40 keV to 120 keV," IEEE Transactions on Nuclear Science, vol. 61, No. 3, pp. 1099-1105, Jun. 2014.

Alvarez, R. et al., "Estimator for Photon Counting Energy Selective X-Ray Imaging with Multibin Pulse Height Analysis," Med. Phys. vol. 38, No. 5, pp. 2324-2334, May 2011.

X-RAY IMAGING BASED ON IMAGE DATA FROM A PHOTON-COUNTING MULTI-BIN X-RAY DETECTOR

TECHNICAL FIELD

The proposed technology generally relates to x-ray imaging and corresponding imaging reconstruction and imaging tasks. In particular, the proposed technology relates to a method of image reconstruction based on image data from a photon-counting multi-bin x-ray detector, and a corresponding image reconstruction system and apparatus for image reconstruction, and a corresponding computer program and computer-program product, as well as apparatus for supporting image reconstruction based on image data from a photon-counting x-ray detector.

BACKGROUND

Radiographic imaging such as x-ray imaging has been used for years in medical applications and for non-destructive testing.

Normally, an x-ray imaging system includes an x-ray source and an x-ray detector consisting of multiple detector elements. The x-ray source emits x-rays, which pass through a subject or object to be imaged and are then registered by the detector. Since some materials absorb a larger fraction of the x-rays than others, an image is formed of the subject or object.

In the electronic read out chain of a direct conversion energy-sensitive multi-bin detector, the interacting x-ray quantum generates a voltage pulse the height of which is proportional to the energy deposited in the sensor by the incident x-ray quantum. This height is compared in a multitude of comparators with tunable voltage settings. These comparator settings are often denoted thresholds and the voltage span between adjacent thresholds defines a so-called bin. When an x-ray deposits energy that results in a voltage pulse falling within a certain bin, a corresponding counter is incremented and this is how energy information is extracted in a photon-counting multi-bin detector.

However, x-ray imaging systems based on photon-counting multi-bin detectors still suffer from artifacts in the reconstructed image and also make material basis decomposition of the spectral data difficult.

There is thus a general demand to improve radiographic imaging such as x-ray imaging.

SUMMARY

It is an object to provide an improved method of image reconstruction.

It is also an object to provide an improved image reconstruction system.

It is another object to provide an apparatus for image reconstruction.

Yet another object is to provide a computer program for use with a photon-counting multi-bin x-ray detector Still another object is to provide a corresponding computer-program product.

It is also an object to provide an apparatus for supporting image reconstruction based on image data from a photon-counting x-ray detector.

These and other objects are met by embodiments of the proposed technology.

According to a first aspect, there is provided a method of image reconstruction based on image data from a photon-counting multi-bin x-ray detector. The method comprises:
  determining parameter(s) of a given functional form of the relationship between comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum;
  performing image reconstruction based on the image data and the determined parameter(s).

According to a second aspect, there is provided an image reconstruction system configured to perform the above method.

According to a third aspect, there is provided an apparatus for image reconstruction based on image data from a photon-counting multi-bin x-ray detector. The apparatus is configured to determine parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum. The apparatus is further configured to perform image reconstruction based on the image data and the determined parameters.

According to a fourth aspect, there is provided a computer program for use with a photon-counting multi-bin x-ray detector. The computer program comprises instructions, which when executed by at least one processor, cause the at least one processor to:
  determine parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum, and
  perform image reconstruction based on image data from the x-ray detector and the determined parameters.

According to a fifth aspect, there is provided a computer-program product comprising a computer-readable medium having stored thereon a computer program as defined above.

According to a sixth aspect, there is provided an apparatus for supporting image reconstruction based on image data from a photon-counting x-ray detector. The apparatus comprises a determination module for determining parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum. The apparatus also comprises an output module for outputting the determined parameters to an image reconstruction system for enabling adjustments in the image reconstruction procedure based on the determined parameters.

In this way, efficient high-quality image reconstruction can be achieved. By way of example, the determined parameter(s) may be used for adjustments in the image reconstruction procedure, e.g. to enable accurate material basis decomposition and/or artifact reduction. This may be important, e.g. in spectral computed tomography.

Other advantages will be appreciated when reading the detailed description.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference designations are used for similar or corresponding elements.

Figure 1:
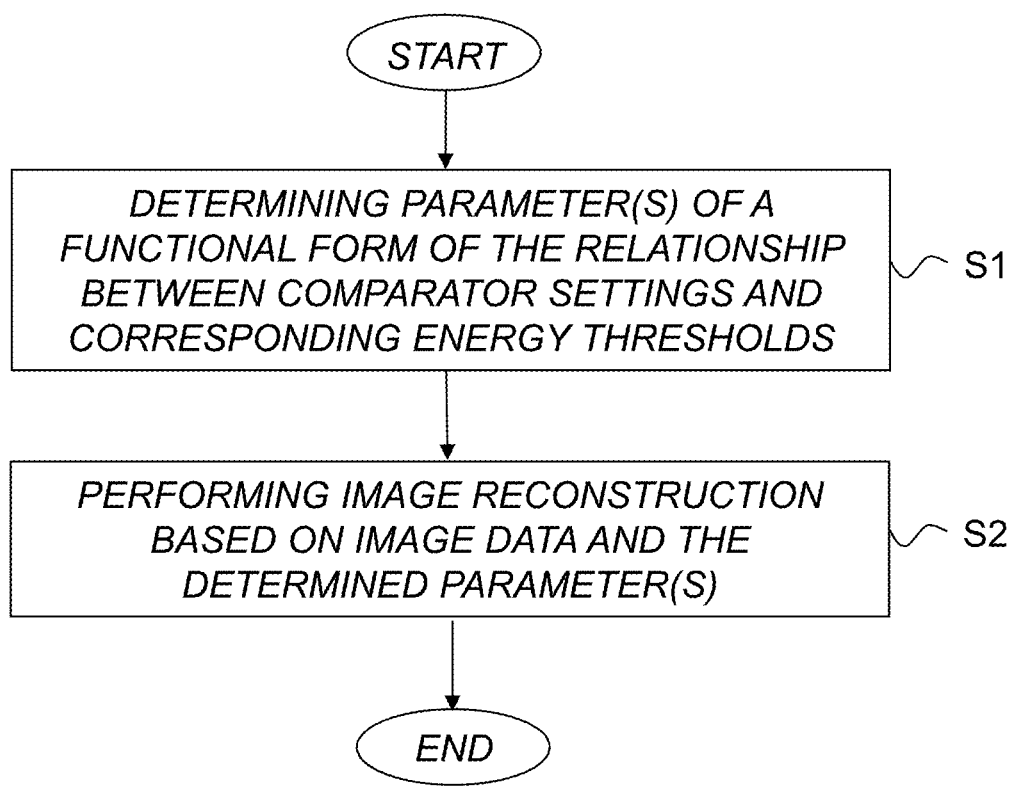
FIG. 1 is a schematic flow diagram illustrating an example of a method of image reconstruction based on image data from a photon-counting multi-bin x-ray detector according to an embodiment.

FIG. 1 is a schematic flow diagram illustrating an example of a method of image reconstruction based on image data from a photon-counting multi-bin x-ray detector according to an embodiment.

The method basically comprises the following steps:

S1: Determining parameter(s) of a given functional form of the relationship between comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum.

S2: Performing image reconstruction based on the image data and the determined parameter(s).

In this way, efficient high-quality image reconstruction can be achieved. By way of example, the determined parameter(s) may be used for adjustments in the image reconstruction procedure, e.g. to enable accurate material basis decomposition and/or artifact reduction. This may be important, e.g. in spectral computed tomography. The determined parameter(s) may be used with any suitable conventional image reconstruction procedure, including e.g. material basis decomposition methods and/or methods for artifact reduction.

For a better understanding of the invention it may be useful to briefly describe a non-limiting example of an x-ray imaging system.

Figure 2:
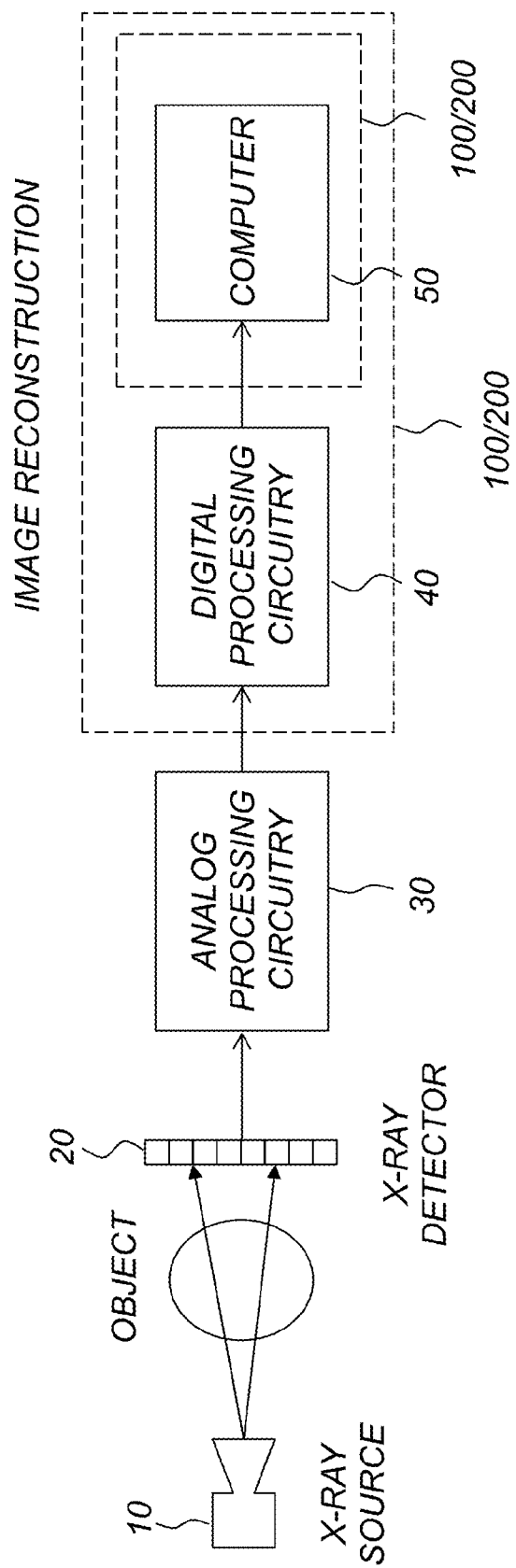
FIG. 2 is a schematic diagram illustrating an example of an x-ray imaging system.

As illustrated in the example of FIG. 2, an x-ray imaging system comprises an x-ray source 10, which emits x-rays; an x-ray detector 20, which detects the x-rays after they have passed through the object; analog processing circuitry 30, which processes the raw electrical signal from the detector and digitizes it; digital processing circuitry 40 which may carry out further processing operations on the measured data such as applying corrections, storing it temporarily, or filtering; and a digital computer 50 which stores the processed data and may perform further post-processing and/or image reconstruction. The overall detector may be regarded as the x-ray detector 20, or the x-ray detector 20 combined with the associated analog processing circuitry 30. The digital part including the digital processing circuitry 40 and/or the computer 50 may be regarded as an image reconstruction system 100/200, which performs image reconstruction based on the image data from the x-ray detector. The image reconstruction system 100/200 may thus be seen as the computer 50, or alternatively the combined system of the digital processing circuitry 40 and the computer 50, or possibly the digital processing circuitry 40 by itself if the digital processing circuitry is further specialized also for image reconstruction.

Figure 3:
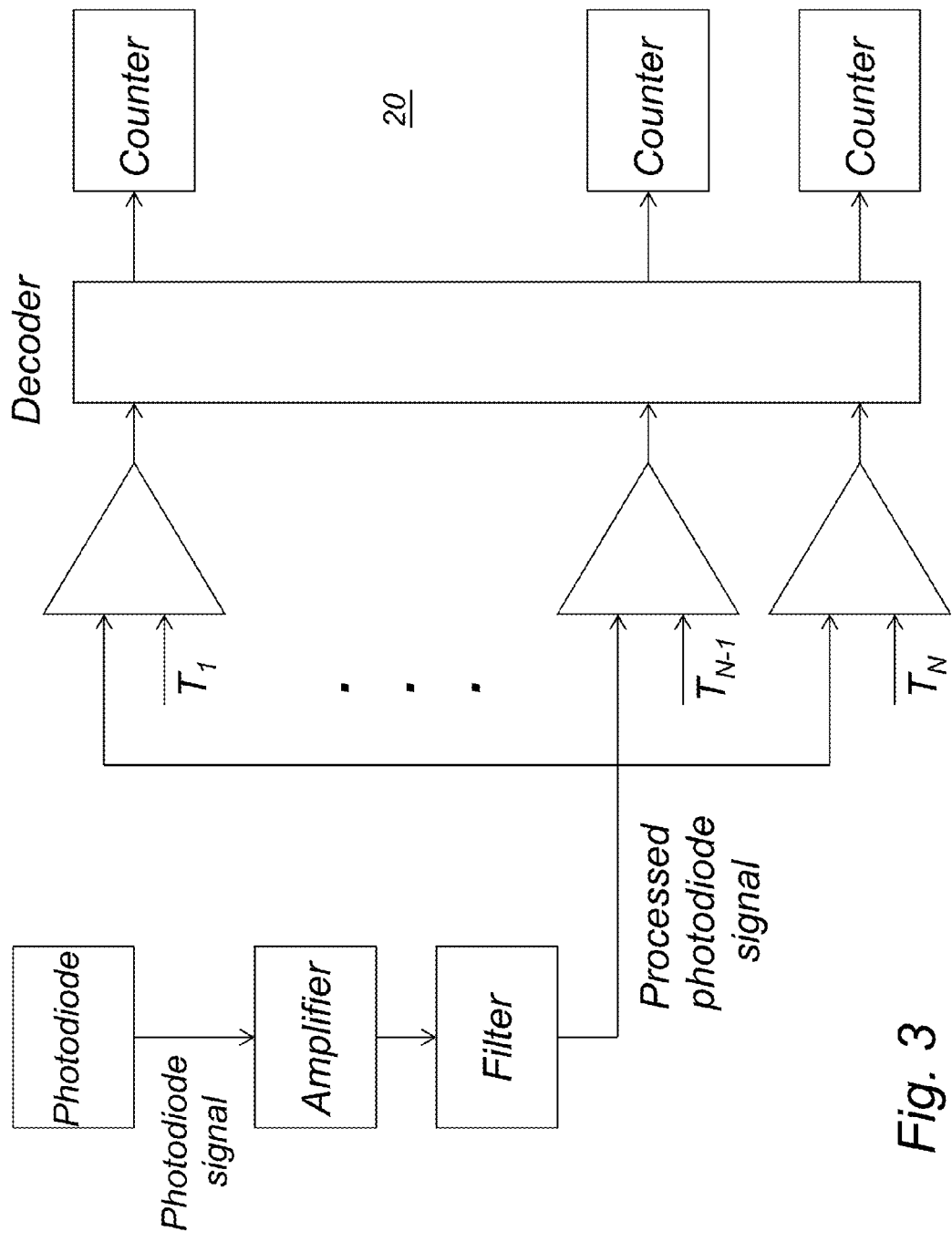
FIG. 3 is a schematic diagram illustrating an example of a photon-counting detector with several energy thresholds.

In a particular example, the detector is a photon-counting detector as shown in FIG. 3 together with associated analog processing electronics. In this example, the detector 20 includes a reverse-biased photodiode where the photons interact and generate current pulses which are amplified by an amplifier and further processed by a filter to attain a desired pulse shape. Each pulse is then compared to a number N of thresholds $T_1, \ldots, T_N$ using comparators, and a decoder circuit processes the comparator output signals and increments one of several counters, corresponding to the highest threshold which is lower than the pulse height. In this way, the incident x-ray spectrum is divided into a number N of energy bins with one counter each counting the number of registered photons in that bin. The counter values form the raw data that is read out from the detector and, possibly after further processing in digital processing circuitry, stored by the computer.

As indicated, the proposed technology provides parameter(s) of a given functional form of the relationship between comparator settings expressed in voltage in the read-out chain of the x-ray detector and the corresponding energy threshold values. Then resulting parameter(s) may then be used in the subsequent image reconstruction procedure.

The proposed technology thus partly relates to a mapping between threshold settings and corresponding energy.

By way of example, the reference pulse height spectrum may be expressed in units of energy and the measured pulse height spectrum expressed in units of voltage.

In a particular example, the first set of data representative of a measured pulse height spectrum is based on a measured x-ray spectrum, and the second set of data representative of a reference pulse height spectrum is based on a previously acquired reference x-ray spectrum or a simulated x-ray spectrum.

For example, the fitting procedure may be performed between a measured accumulated x-ray spectrum and a simulated accumulated x-ray spectrum, taking physical detector characteristics into consideration in the simulation.

Alternatively, the fitting procedure may for example be performed between a measured accumulated x-ray spectrum and a previously acquired accumulated x-ray spectrum.

In a particular example, the first set of data representative of a measured pulse height spectrum corresponds to a differentiated version of a measured accumulated x-ray spectrum, and the second set of data representative of an accumulated reference pulse height spectrum corresponds to a differentiated version of the accumulated reference x-ray spectrum.

For example, a measured accumulated x-ray spectrum, and a corresponding reference accumulated x-ray spectrum may be differentiated, and the fitting procedure may then be performed between the differentiated measured accumulated x-ray spectrum and the differentiated accumulated reference x-ray spectrum.

Optionally, the number of measurement points and their setting in voltage are chosen so that the corresponding differentiated x-ray spectrum is a histogram of counts in each detection bin, and the parameter(s) is/are determined based on histogram data for each of a number of channels in the read-out chain of the x-ray detector and corresponding reference histogram data.

By way of example, a broad x-ray spectrum of the x-ray source associated with the imaging modality is used to acquire an accumulated spectrum of counts as a function of comparator voltage, and the first set of data representative of a measured pulse height spectrum is based on the acquired accumulated spectrum of counts.

With regard to the parameter(s) of the functional form of the relationship between comparator settings expressed in voltage in the read-out chain of the x-ray detector and the corresponding energy threshold values, different options exist.

By way of example, the parameter(s) may include an array $p_i$ of one or more parameters relating the voltage $U_i$ of the measured pulse height spectrum with the energy $E_i$ of the reference pulse height spectrum according to:

$$U_i = f(E_i; p_i),$$

where f is a given function and the subscript i denotes a particular read-out channel.

As an example, the parameters may include gain $g_i$ and offset $m_i$ relating the voltage $U_i$ of the measured pulse height spectrum with the energy $E_i$ of the reference pulse height spectrum according to:

$$U_i = g_i E_i + m_i,$$

where the subscript i denotes the read-out channel.

For example, the fitting procedure may be performed for each of a number of channels in the read-out chain of the x-ray detector.

In the following, the proposed technology will be described with reference to various non-limiting examples. It should though be understood that the invention is not limited thereto.

As discussed, in the electronic read out chain of direct conversion energy sensitive multi-bin detectors the interacting x-ray quantum generates a voltage pulse the height of which is proportional to the energy deposited in the sensor by the incident x-ray quantum. This height is compared to a multitude of comparators with tunable voltages. These comparators are denoted thresholds and the voltage span between adjacent thresholds defines a bin. When an x-ray deposits energy that results in a voltage pulse falling within a certain bin, the corresponding counter is incremented and this is how energy information is extracted in a photon counting multi-bin detector.

The tunable comparators or thresholds are set in millivolts. For the same deposited energy in the sensor (typically in the range of 30-140 keV), inhomogeneities in the electronic components result in slightly different pulse heights in millivolts. Typically each channel presents a linear relationship between deposited energy in keV and the pulse height. For channel i it thus holds that a deposited energy E (keV) results in a peak amplitude of $U_i$ (mV), where:

$$U_i = g_i E + m_i \tag{1}$$

and $g_i$ (mV/keV) and $m_i$ (mV) are the gain and offset, respectively, of channel i. It is understood that although the functional form in Eq. (1) is linear in E, it is but a small and trivial step to assign a different functional form of the relationship and the methods, results and claims presented herein are equally valid for other parameterized functional forms.

Figure 4:
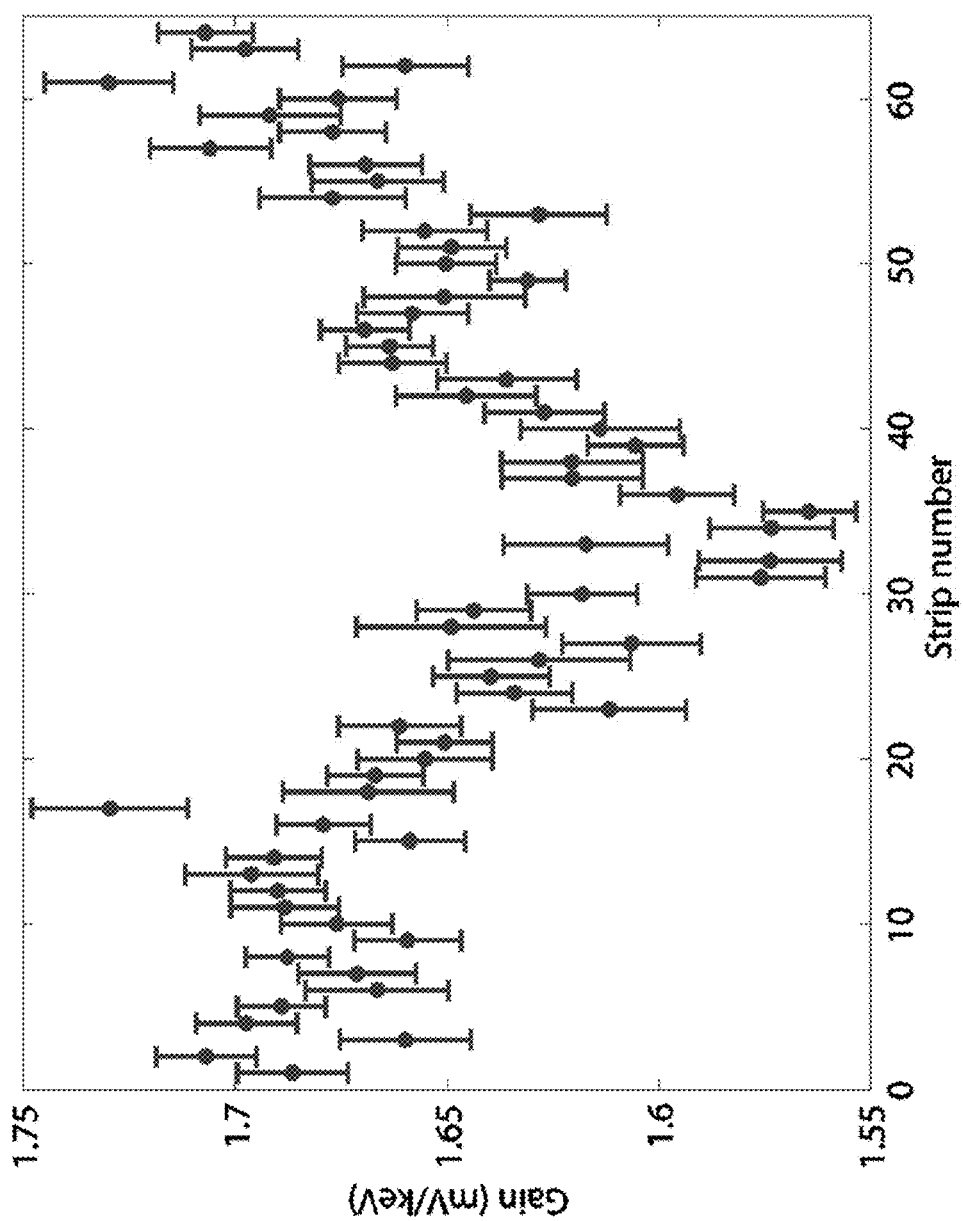
FIG. 4 is a schematic diagram illustrating an example of how gain values as determined from multiple s-curve scans with monochromatic rays of different energy differ between channels, where the error bars indicate the statistical uncertainty.
Figure 5:
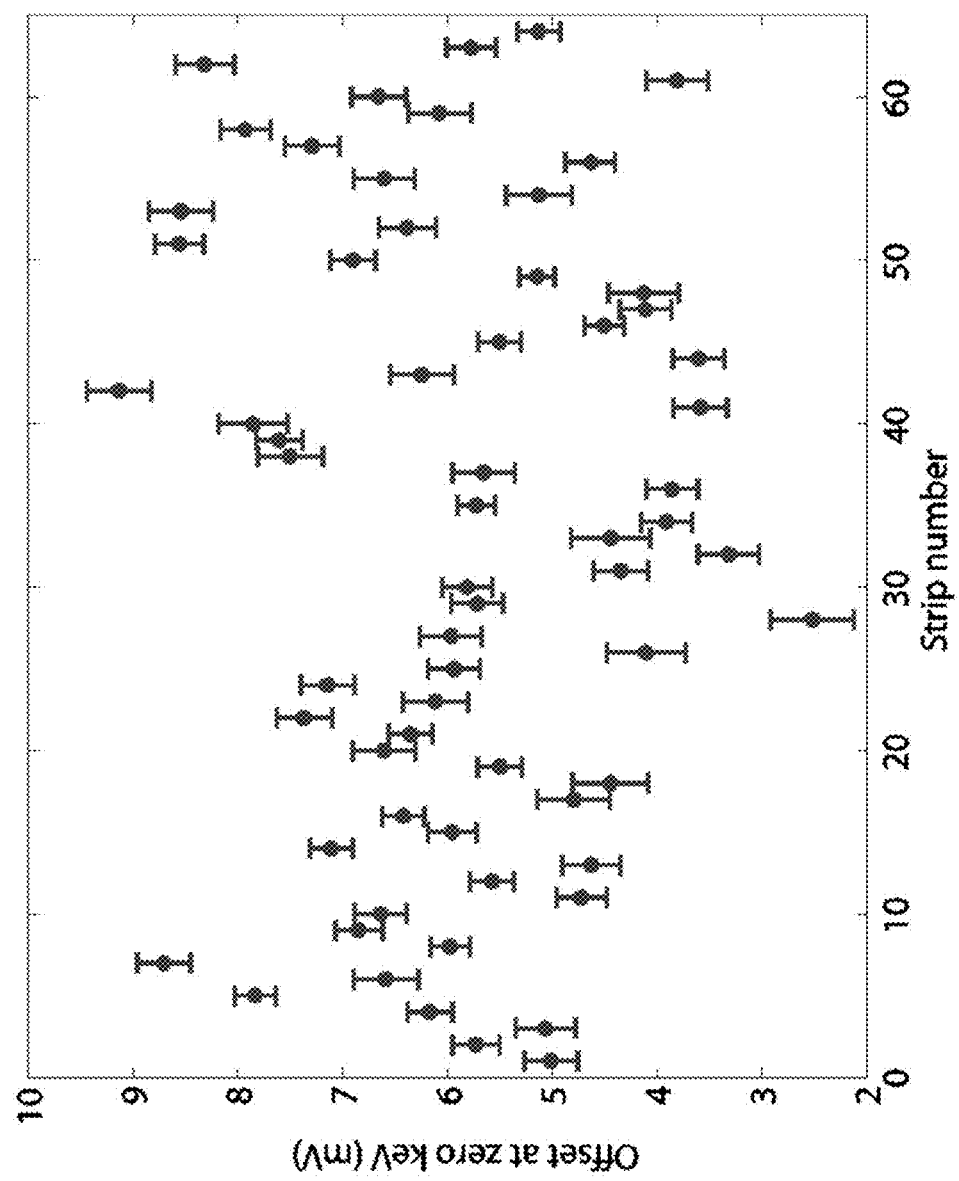
FIG. 5 is a schematic diagram illustrating an example of how offset values as determined from multiple s-curve scans with monochromatic rays of different energy differ between channels.

The gain and the offset can differ between channels as illustrated in FIG. 4 and FIG. 5. Reference can be made to, e.g. C. Xu et al. "*Evaluation of a second-generation ultrafast energy-resolved ASIC for photon-counting spectral CT*" IEEE Transactions on Nuclear Science, vol. 60, no. 1, pp. 437-445, February 2013. An event depositing E in channel i results in a pulse amplitude $U_i$ whereas in channel j an amplitude $U_j$ is obtained. If an internal threshold T is located such that $U_i < T < U_j$, or $U_j < T < U_i$, the same energy photon will result in a signal in different bins in different channels (pixel location). This will result in ring artifacts in the reconstructed image and also make material basis decomposition of the spectral data difficult.

Ring Artifacts

One method to remove ring artifacts is by means of post processing the sinogram or the reconstructed image; in essence an algorithm searches for stripes or circles and applies some correction scheme on the thus identified pixels. Another method to reduce is to "reshuffle" the raw counts among the bins using an affine transformation. This is described, e.g. in reference: M. Persson and H. Bornefalk, "*A Framework for Evaluating Threshold Variation Compensation Methods in Photon Counting Spectral CT*", IEEE Transactions on Medical Imaging, vol. 31, no. 10, pp. 1861-1874, October 2012. While more direct (as no search of relative contrast changes is performed as in post-processing methods) the method either requires excessive calibration measurements, where the relative spectral response of all channels is determined for a multitude of combinations of x-ray spectral shape, tissue combinations and thicknesses, or the method requires accurate knowledge of the thresholds for each channel in keV. Utilizing the latter information the spectral response, i.e. distribution of counts across the bins, can be derived using a typical so called forward model of the imaging system where the expected number of counts in bin k, $\lambda_k$, after passage through an object with distribution of linear attenuation coefficients $\mu(r; E)$ is given by:

$$\lambda_k(x',\theta)=N_0\int_0^\infty \Phi(E)D(E)S_k(E)\exp(-\int_l \mu(r;E)ds)dE \text{ with } S_k(E)=\int_{T_{k-1}}^{T_k} R(E,E')dE' \quad (2)$$

In Eq. (2) r is the position vector, $\{T_k\}$ the set of thresholds in keV, $\Phi(E)$ the x-ray spectrum (number of photons per unit energy), R(E, E') the energy response function of the detector (such that R(E, E') denotes the probability of an incident x-ray photon of energy E deposits energy E' in the detector). $N_0$ is the unattenuated fluence directed towards the detector element x' at rotation angle $\theta$. Details can be found in reference: E. Roessl and R. Proksa, "*K-edge imaging in x-ray computed tomography using multi-bin photon counting detectors*", Phys. Med. Biol. 52 (2007) 4679-4696.

Material Basis Decomposition

In basis decomposition techniques applied to energy resolved CT the goal can be to break down the content of each voxel V(r) into soft tissue content, bone content and lipid content. Such a break down can be beneficial for Monte Carlo based dose planning programs and has the potential to improve dose planning for radiation treatment purposes.

A second use of basis decomposition, also well known to those skilled in the art, is to reconstruct the entire energy dependence of the linear attenuation coefficient of each voxel.

Whereas standard energy integrating CT reconstructs the linear attenuation coefficient at each voxel at some average energy $\hat{E}$ the use of the Ansatz that $\mu(r; E)$ is written as a separable linear combination of two or more known energy bases:

$$\mu(r;E)=a_1(r)f_1(E)+a_2(r)f_2(E) \quad (3)$$

can be used in the forward model (2) to develop a maximum likelihood (ML) solution to the line integrals $A_i=\int a_i ds$, i.e.

$$A_1^*,A_2^*=\arg\max_{A_1,A_2} P(\{m_i\};A_1,A_2)=\arg\min_{A_1,A_2} \Pi_{i=1}^N(\lambda_i - m_i \log \lambda_i) \quad (4)$$

where $\{m_i\}$ are the recorded counts in bins i=1, ..., N and the $\lambda_i$'s are from the forward model (2).

After $A_i^*$ has been determined for all angles $\theta$ and detector positions t, $a_i$ can be determined via an implementation of the inverse radon transform (in tomographic imaging) to generate the ML estimates of $a_1^*$ and $a_2^*$. This method is well described in the literature, for instance in reference E. Roessl and R. Proksa, "*K-edge imaging in x-ray computed tomography using multi-bin photon counting detectors*", Phys. Med. Biol. 52 (2007) 4679-4696, and results in a full energy characterization of the linear attenuation coefficients:

$$\mu^*(r;E)=a_1^*(r)f_1(E)+a_2^*(r)f_2(E). \quad (5)$$

The expression $\mu^*(r; E)$ of Eq. (5) can for instance be used for displaying synthetic monoenergetic images by selecting a display energy E" and insert in Eq. (4). This is a popular method for contrast enhancement and is implemented on the work stations of some CT vendors.

If the ML method is going to be used for accurate material decomposition, the parameters of the forward model (2) have to be known with a high degree of certainty. The same holds for the determination of the affine transformation to remove ring artifacts in energy weighting schemes as described in reference M. Persson and H. Bornefalk, "*A Framework for Evaluating Threshold Variation Compensation Methods in Photon Counting Spectral CT*", IEEE Transactions on Medical Imaging, vol. 31, no, 10, pp. 1861-1874, October 2012.

In particular $\{T_i\}$, the set of thresholds in keV, need to be known accurately. For detector prototypes these thresholds can be determined with arbitrary accuracy by threshold scans utilizing synchrotron radiation, as set forth in reference Liu et al, "*A silicon-strip detector for photon-counting spectral CT: energy resolution from 40 keV to 120 keV*," IEEE Transactions on Nuclear Science, 61(3):1099-1105, 2014, or with radioactive isotopes. In such a threshold scan (also known as s-curve measurement), the threshold is initially set to a high value resulting in zero registered counts since the monochromatic radiation results in pulses lower than the threshold. It is then lowered stepwise (in digital-to-analog converter (DAC) setting or mV) and the counts at each threshold are registered. When the there is no increase in counts any more the procedure is discontinued and the result is an s-curve as in FIG. 6.

The dots are measurements and the solid line is fitted to the data. Given a constant flux and detector read out time, the number of detected counts will increase as the threshold is decreased. The point on the x-axis that corresponds to the point on the curve with the steepest slope is the threshold that corresponds to the particular monoenergetic energy applied.

The value at the x-axis of the point of maximum slope corresponds is the DAC-setting or mV that corresponds to the monochromatic beam energy. If the beam energy is now changed and the procedure repeated, the DAC-settings or threshold voltages that correspond to a range of monochromatic beam energies can be determined from which the gain and offset of Eq. (1) can be determined from a linear regression.

The above method is time consuming and difficult to perform in clinical routine. CT-detectors are known to drift over time (for instance the set of thresholds $\{T_i\}$ for each channel can change somewhat from day-to-day). For that reason it is common practice to perform a detector calibration each morning. Since high-flux monochromatic radiation sources are not readily available in the clinics there is a need for an accurate method of threshold determination or, equivalently, determining the gain and threshold of each channel according to Eq. (2), utilizing something other than monochromatic x-ray radiation.

Preferably, one would want to use the x-ray spectrum of the existing x-ray tube attached to the system. Thus far, this has not been possible and instead one has had to revert to the use of calibration phantoms. The main idea in methods based on calibration phantoms is to obtain several x-ray exposures with differently composed objects in the beam path. Typically two or three basis materials are used with varying thicknesses. In the below example two basis functions $f_1(E)$ and $f_2(E)$ are used but the method is easily extended to higher dimensionality.

Let $[c_{1,0}, c_{2,0}, c_{3,0}, \ldots, c_{N,0}]^T$ be the unattenuated counts in each bin 1, 2, 3, ..., N during a measurement and $[c_{1,l}, c_{2,l}, c_{3,l}, \ldots, c_{N,l}]^T$ the counts in measurement j. The vectors of projections:

$$\left[-\log\left(\frac{c_{1,l}}{c_{1,0}}\right), -\log\left(\frac{c_{2,l}}{c_{2,0}}\right), -\log\left(\frac{c_{3,l}}{c_{3,0}}\right), \ldots, -\log\left(\frac{c_{N,l}}{c_{N,0}}\right)\right]^T$$

are then formed. The purpose of the calibration is to, for each detector channel, determine the function F that relates the projections to the line integrals:

$$\left[\int_l a_1(E)ds, \int_l a_2(E)ds\right] = F\left(\left[-\log\left(\frac{c_{1,j}}{c_{1,0}}\right),\right.\right.$$
$$\left.\left.-\log\left(\frac{c_{2,j}}{c_{2,0}}\right), -\log\left(\frac{c_{3,j}}{c_{3,0}}\right), \ldots, -\log\left(\frac{c_{N,j}}{c_{N,0}}\right)\right]^T\right) \quad (6)$$

If F is linear (a matrix) the system (6) can be solved in the least squares sense.

Other functional forms have been suggested (polynomials) and variations of the method are described in at least the following publications:

T. G. Schmidt, "*An empirical method for correcting the detector spectral response in energy-resolved CT,*" in Medical Imaging 2012: Physics of Medical Imaging, Proc. SPIE 8313, 831312, SPIE 2012.

R. E. Alvarez, "*Estimator for photon counting energy selective x-ray imaging with multi-bin pulse height analysis*" in Medical Physics, 38 (5), May 2011, p 2324

S. Lee et al, "*Quantitative material decomposition using spectral computed tomography with an energy-resolved photon-counting detector*", Physics in Medicine and Biology, vol 59(18), p. 5457

J. Jakubek, "*Data processing and image reconstruction methods for pixel detectors,*" Nucl. Instr. and Meth. A, vol. 576, no. 1, pp. 223-234, June 2007, proceedings of the 8th International Workshop on Radiation Imaging Detectors.

Other examples of related prior art include:

U.S. Pat. No. 7,756,239 relates to a calibration procedure for multi-bin spectral x-ray imaging based on measuring the response in a plurality of energy bins of different combinations of materials and thicknesses and relating the bin response to the line integrals of the materials.

U.S. Pat. No. 8,422,636 relates to a procedure in which discriminator thresholds are set in mV or DAC settings and shifting the thresholds relative to each other in order to minimize noise in the bin images.

U.S. Pat. No. 7,983,397 relates to a method and apparatus for determining one or more characteristics of radiation based on a calibration operation to determine a transform from measured counts in bins to an estimate of the absorbed dose.

U.S. Pat. No. 8,000,434 relates to method of reconstructing an energy spectrum that is distorted from charge sharing.

US 2014/0105369 relates to a calibration apparatus and method that may be used for setting a magnitude of an electric pulse based on a result obtained by imaging at least one imaging object, and that may be used for mapping and calibrating a photon energy corresponding to an absorption edge of at least one calibration object.

JP 2011/085479 relates to a calibration device for photon counting type radiation detector and calibration method thereof based on computing a threshold with equalizing detection sensitivity for radiation of elements.

US 2013/0301798 relates to a calibration method of a radiation detecting apparatus, a control method of a radiation imaging apparatus and a radiation imaging apparatus. The control method of the radiation imaging apparatus includes performing prior information acquisition by obtaining at least one correction threshold energy, at which a theoretical radiation intensity of at least one threshold energy is measured, and performing radiation image acquisition by obtaining at least one radiation image at the at least one threshold energy using the at least one correction threshold energy.

According to an example embodiment of the proposed technology, parameters such as gain and offset for each channel can be accurately determined, e.g. using the broad x-ray spectrum of the x-ray imaging modality. The method is robust and also fast and can therefore be performed in daily routine. The method allows the comparator thresholds to first be set in millivolts or DAC-values and the exact corresponding threshold in kilo electron volts (keV) can then be determined from Eq. (1). With accurate knowledge of individual channel thresholds, the material basis decomposition can be performed using the forward model of Eq. (2) and there is no reason to revert to procedures that utilize physical calibration phantoms.

An alternative but more time consuming method of mapping the internal thresholds against x-ray photon energy is to use several exposures with different applied x-ray tube acceleration voltages. It is then possible to scan a threshold from a low setting to a higher and note the threshold setting when the detected fluence suddenly drops to zero; the last threshold that registered counts then corresponds to an x-ray energy equal to the x-ray tube acceleration voltage multiplied with the charge of one electron (if the acceleration voltage is 100 kV the threshold corresponds to 100 keV). This method however requires multiple threshold scans for many different x-ray spectra.

In another example embodiment, there is no need for a threshold scan and instead the spread among the different energy bins is used to infer gain and offset (according to Eq. (1)) for each channel.

In a non-limiting example embodiment, there is provided a method to determine parameters such as the gain and offset of individual detector channels by fitting a reference pulse-height spectrum to a measured pulse height spectrum. The measured spectrum may be obtained by scanning a comparator threshold across a range of pulse height amplitudes, resulting in an accumulated x-ray spectrum in units of mV (denoted S-curve). In a preferred embodiment, the reference spectrum is tabulated. Such tabulation can be achieved by means of either detailed Monte Carlo simulations that takes into account the physical characteristics of the detector, such as charge sharing, response function, detection efficiency, pileup etc, or by measuring the x-ray spectrum with a reference detector. In another embodiment, parts of the reference spectrum is generated in real time using the known detector characteristics as input.

The measured pulse height spectrum will differ from the reference spectrum in two ways; the amplitude and the scale of the abscissa. Whereas the simulated spectrum is determined in units of keV the measures is in units of mV or comparator settings (DAC). This allows a fitting procedure of the measured data to the reference data with three free parameters; an amplitude scale factor and the gain $g_i$ and offset $m_i$ relating the coordinate $U_i$ (in mV or DAC) of the abscissa of the measured pulse height spectrum with the energy E of the reference spectrum: $U_i = g_i E + m_i$. Subscript i indicates that the fitting procedure is carried out individually for each channel i. The exact nature of the fitting procedure is not important; the least squares method and maximum likelihood methods are two popular choices.

Figure 6:
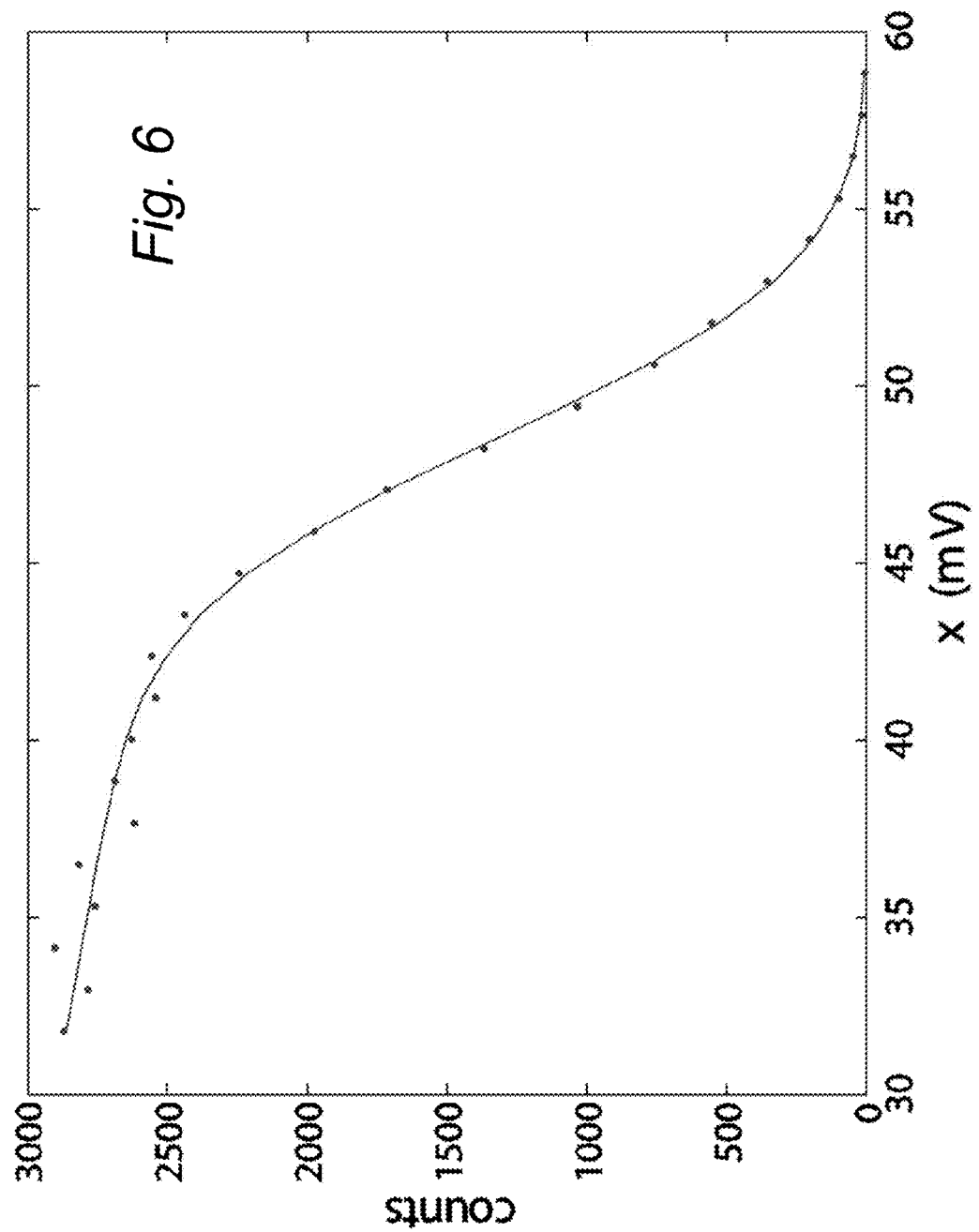
FIG. 6 is a schematic diagram illustrating an example of the result of a threshold scan of a monochromatic source.

In this particular example, a method to determine the gain and offset according to Eq. (1) is disclosed whereby the parameters $g_i$ and $m_i$ of each channel i is determined by adjusting a simulated pulse-height spectrum to a measured one. The measured spectrum is obtained by scanning a comparator threshold across the range of detectable pulse amplitudes given a specified x-ray input spectrum (typically assumed a 120 kVp Tungsten spectrum with added aluminum filtration). At each scanned threshold position, expressed in a voltage in mV or a DAC setting, the total number of counts above threshold is accumulated during a fixed measurement time, resulting in an integral spectrum in units of mV (FIG. 6).

In a preferred embodiment of the invention a simulated spectrum is generated with the aid of a detailed Monte Carlo simulation that takes into account all physical characteristics of the x-ray imaging chain. These include but are not limited to x-ray spectrum, detection efficiency, charge sharing, flux and accompanied pileup, possible fluorescent emission, incomplete charge collection, object scatter, detector response function, diode misalignment, electronic noise and interaction depth in the detector as captured by the depth segment number. The total number of x-ray events simulated is left as an open parameter (scale factor), affecting only the amplitude of the accumulated pulse height spectrum.

Figure 7:
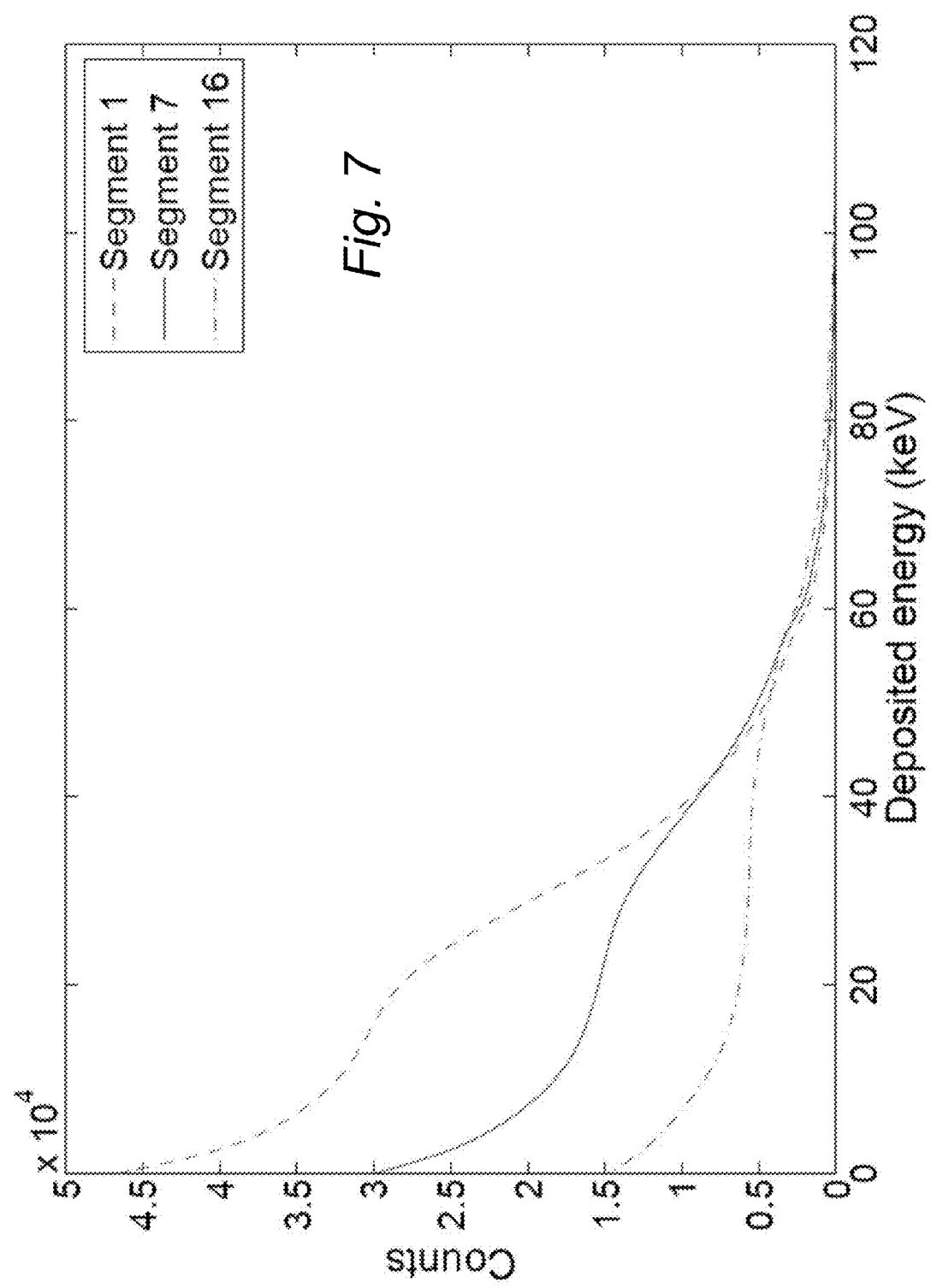
FIG. 7 is a schematic diagram illustrating an example of cumulative (integrated) spectra of deposited energies, as obtained in three different depth segments.

The simulated photon interactions are used to form an integral spectrum of deposited energies in units of keV (FIG. 7). Note that low energy photons are preferentially absorbed in the top layer, with segment number 1.

Equation (1) now directly represents the relationship between the abscissae of the measured and simulated spectrum, such that gain and offset (and the amplitude scale factor) can be estimated using a fitting procedure. Several such fitting procedures are possible; the least squares, the weighted least square and the maximum likelihood are all common and plausible choices. Below we show how the weighted least squares method can be implemented.

Figure 8:
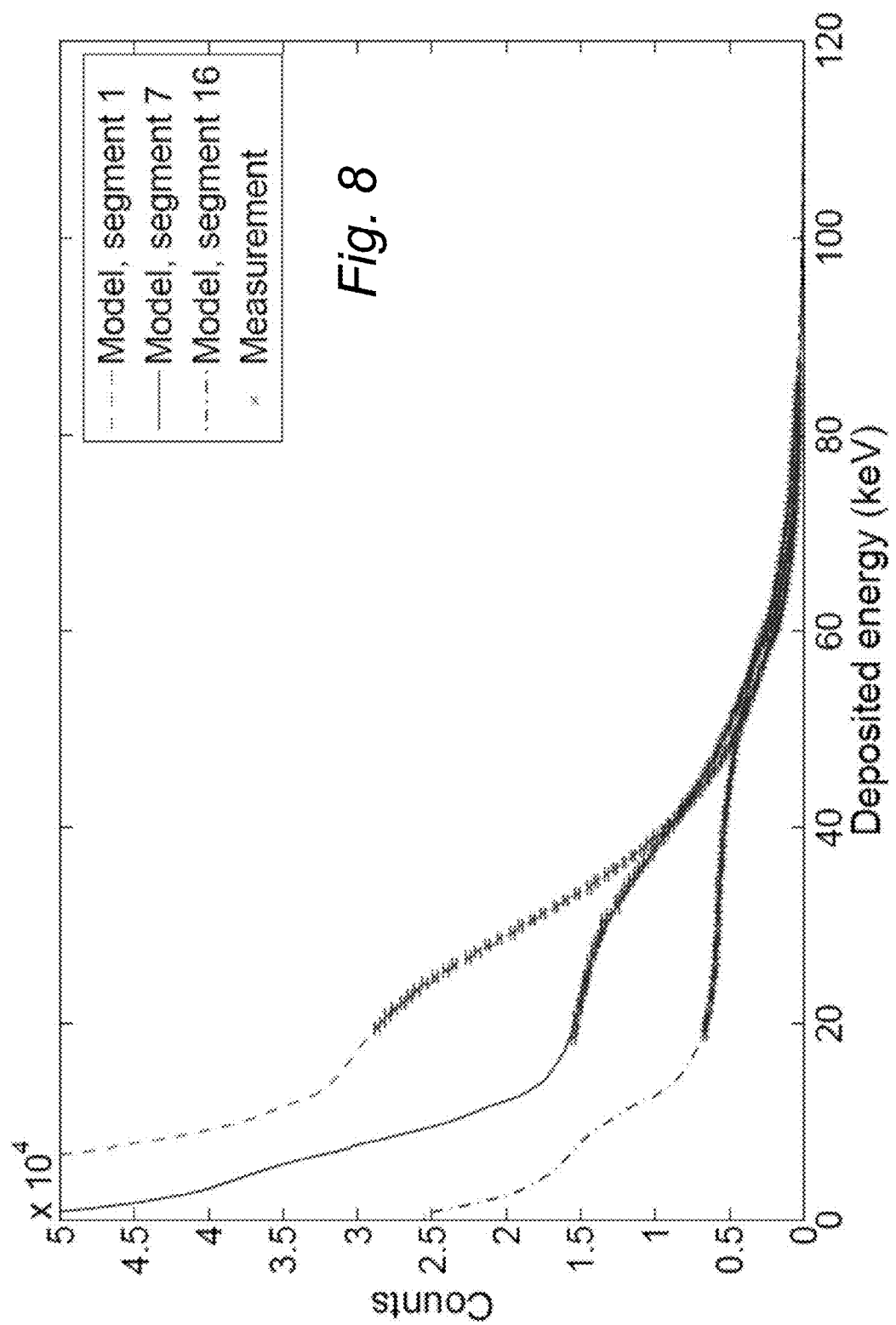
FIG. 8 is a schematic diagram illustrating an example of a particular measured accumulated pulse-height spectra and corresponding fitted models for three segments.

Let $\{x_l^{mV}, y_l\}$ be the set of measured data points of FIG. 8. The scale of the x-axis corresponds to the keV-scale of the model. This means that $\{x_l^{mV}\}$ are the threshold settings in mV (or possible DAC settings) and $\{y_l\}$ the corresponding counts above the threshold. l is a measurement index ranging from 1 to the maximum number of measurements performed. Now let the function $F(x^{keV}; \{\varphi_j\}_i, g_i, m_i)$ capture the complete forward equation of a particular detector channel i and return the number of counts above threshold $x^{keV}$ (in kiloelectronvolts, keV) given the parameters $\{\varphi_j\}$, $g_i$, $m_i$. The set $\{\varphi_j\}_i$ comprises all forward model parameters characteristic for channel i, such as detection efficiency, threshold setting in mV, charge sharing, scatter, depth segment, etc and are assumed to be known (as in the case of applied voltage to the comparators to determine the thresholds in mV) or to follow first principles as common in Monte Carlo simulation work (for the detection efficiency). Note that parameters will differ from channel to channel due to inhomogeneities such as different degree of electronic noise, possible misalignment of sensor diodes etc.

The weighted least squares optimization problem for each channel can now be expressed as:

$$g_i^*, m_i^* = \operatorname{argmin}_{g_i, m_i, \alpha} \Sigma_l y_l^{-1} \left( y_l - \alpha F\left( \frac{x_l^{mV} - m_i}{g_i}; \{\phi_j\}_i \right) \right)^2 \quad (7)$$

where α is a scale factor dependent on x-ray flux and measurement window time. Note that Eq. (1) has been applied inside the argument of F to transform the known threshold in mV to keV. The $y_l^{-1}$ term is the reciprocal of the variance of the counts (due to Poisson statistics) and applied to weight the data points.

In another embodiment of the invention a multitude of x-ray spectra (for instance varying kVp, filter thickness and material and flux) have been collected by a reference detector (acting as ground truth) and stored in lookup tables. In such an embodiment a previously acquired spectrum is used for the function F in Eq. (7), effectively mapping measured accumulated spectra to a common default accumulated spectra thereby achieving the goal of minimizing the effect of channel-to-channel differences.

Figure 9:
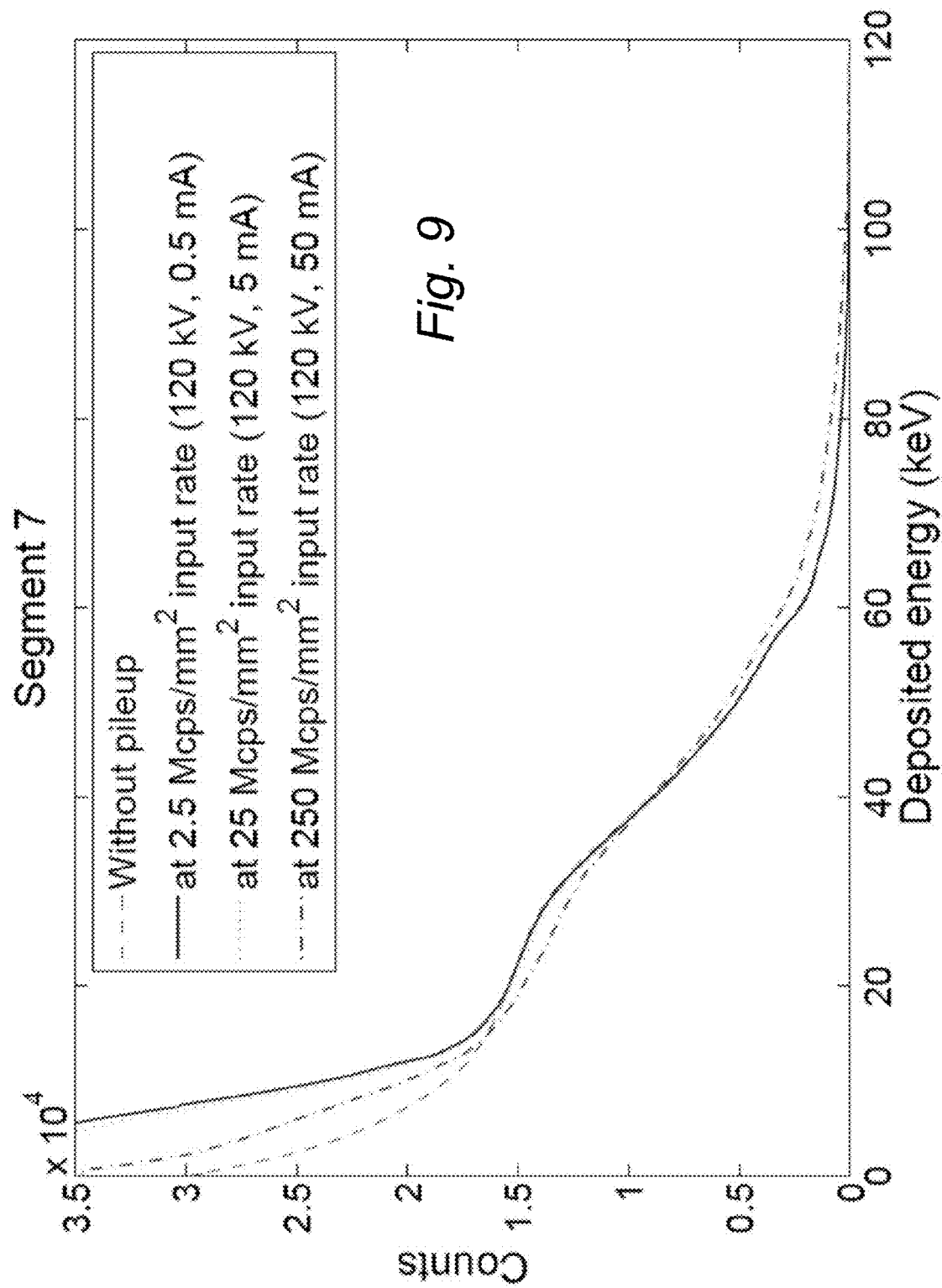
FIG. 9 is a schematic diagram illustrating an example of a cumulative (integrated) spectra of deposited energies with and without pileup effect.

In FIG. 9 the effect of high flux on pileup, and the resulting shift of the accumulated spectrum, is shown. Three x-ray spectra with input count rates of 2.5 Mcps/mm², 25 Mcps/mm² and 250 Mcps/mm² are used. This particular illustration shows the distributions are shown for segment 7.

In FIG. 7, the dependence of interaction depth in the sensor diode is shown (for larger segment numbers, i.e. deeper interaction location, the spectrum is shifted toward higher energies a mechanism commonly denoted beam hardening). The results of the actual fitting procedure are shown in FIG. 8, showing an excellent agreement between the simulated and measured spectra.

Any misspecifications of the parameter set $\{\varphi_j\}_i$ will result in biased estimates of $g_i^*$ and $m_i^*$. If the necessary forward model parameters $\{\varphi_j\}_i$ cannot be estimated to a good enough precision, such a bias could render the entire procedure inapplicable. However, the extent of the bias can easily be estimated from known uncertainties. This is done in the following fashion. Let $f$ be the vector valued function implicit in Eq. (7), i.e. the function that takes all measurements l=1, 2, 3, . . . and model specifications as input and returns the estimates $g_i^*$ and $m_i^*$. Denote the measurements X (i.e. the data set $\{x_l^{mV}, y_l\}$) and the parameter estimates for channel i $\{\varphi_j\}_i$. Let all default parameter settings for channel i be collected in the set $\{\varphi_j^0\}_i = \{\varphi_1^0, \varphi_2^0, \ldots, \varphi_j^0, \ldots\}_i$. The partial derivatives with respect to the parameters are estimated by $$\left( \frac{\partial g_i^*}{\partial \phi_j}, \frac{\partial m_i^*}{\partial \phi_j} \right) = \frac{f(X; \{\phi_1^0, \phi_2^0, \ldots, \phi_j^0 + \Delta\phi_j, \ldots\}_i) - f(X; \{\phi_1^0, \phi_2^0, \ldots, \phi_j^0, \ldots\}_i)}{\Delta \phi_j} \quad (8)$$

and, since the parameter errors are independent, the total systematic error can be estimated as $$\sigma_{g_i}^2 = \Sigma_j \left| \frac{\partial g_i^*}{\partial \phi_j} \right|^2 \sigma_j^2 \quad (9)$$

where the symbol $\sigma^2$ indicates that a Gaussian distribution of uncertainties is assumed and that the resulting variance, or mean squared error, is estimated, $\sigma_j^2$ is the estimated variance (mean square error or the parameter estimate) for parameter j in $\{\varphi_j\}_i$. Typical values are obtained from the manufacturer, for instance the x-ray tube acceleration voltage might be 1 keV off, making $\varphi_j^0=120$ kV and $\Delta\varphi_j=1$ kV for the particular j that corresponds to the acceleration voltage. Similarly, tabulated linear attenuation coefficient needed for deriving the detection efficiency of the detector material is stated to have an error in the order of 1%. When textbook methods of error propagation are used, feeding the errors through $$x^{keV} = \frac{x^{mV} - m_i^*}{g_i^*}, \quad (10)$$

the typical resulting bias in a threshold $x_i^{keV}$ set in keV, is in the order of 0.1-0.2 keV. In a recent publication (Bornefalk et al., "*Necessary forward model specification accuracy for basis material decomposition in spectral CT*"), this has been shown to be within the tolerable limit where errors introduced in the $A_1^*$ and $A_2^*$-estimates of Eq. (4), via the bias of the thresholds denoted $T_k$ in Eq. (2), is below the uncertainty introduced by the statistical nature of photon interaction. Thus it is clear that the above disclosed method for determining thresholds in keV, via gain and offset determination from a broad x-ray spectrum scan, has the potential to be accurate enough to be used in clinical applications.

Naturally, bias in the estimated keV-thresholds might not be the only limitation to the practical usefulness of the technique. The variance (i.e. statistical uncertainty around the bias) may affect the ability to produce meaningful estimates. However, under typical x-ray exposure settings a mere one to two seconds of x-ray exposure for each mV-threshold setting $x_i^{mV}$ is needed to push the statistical component of the total threshold uncertainty down to close to zero.

Figure 10:
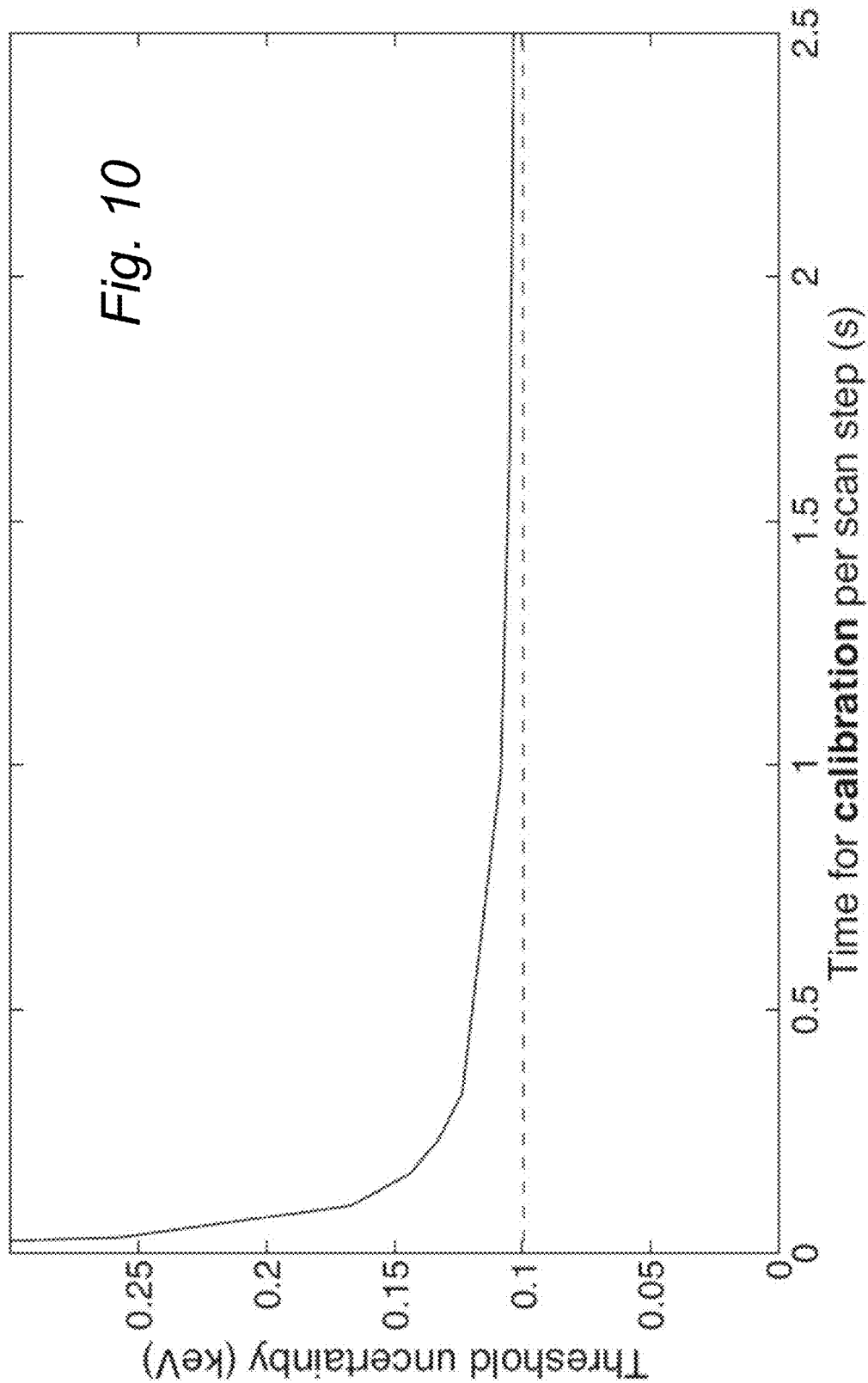
FIG. 10 is a schematic diagram illustrating an example of the threshold uncertainty as a function of measurement time per scan step, evaluated for a systematic uncertainty of 0.1 keV.

This is illustrated in FIG. 10 and indicates that the method not only has the capability to determine photon counting multi-bin spectral CT thresholds accurately enough, but also quickly, such that a the entire procedure can be carried on in a matter of minutes and thus allow careful recalibration of energy threshold in the clinical routine, a key advantage to other methods requiring time consuming procedures. Using a calibration time of 2 second per 1-keV scan step at the particular count rate used in the simulations resulting in this result, the statistical contribution is negligible and the keV-uncertainty of a calibrated threshold is only limited by systematics.

A slight verification of the described procedure would be to acquire not accumulated spectra as in FIG. 6 through FIG. 9, but instead use the distribution-like function of the x-ray energies (i.e. the differentiated version of the accumulated spectrum). If such a method is used, and the electronic comparator values applied ($x^{mV}$) are fixed and equal in number to the number of comparators/bins in the system, it is clear that the measured spectrum would correspond to a histogram of counts in each bin. Since gain and offset would differ between channels, and comparator settings are applied globally, one would expect the histograms of bin counts to differ from channel to channel. Using Eq. (2), the forward model could be changed to encompass the free parameters $g_i$ and $m_i$ of each channel, i.e. setting $$S_k(E) = \int_{(U_{(k-1)} - m_i)/g_i}^{(U_k - m_i)/g_i} R(E, E') dE' \quad (11)$$

where $U_k$ is the externally applied comparator setting in mV which via Eq. (1) is converted to a corresponding energy threshold setting in keV. Fitting the measured histogram data to simulated data using Eq. (2), and keeping $m_i$ and $g_i$ as free parameters, is therefore clearly a closely related implementation to the disclosed invention. The difference lies only in differentiating the s-curve measurement and selecting the sampling points $\{x_i^{mV}\}$ such that they coincide with the desired bin edges. After such a reformulation of the optimization problem, the solution follows the same outline as above.

It will be appreciated that the methods and devices described herein can be combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Particular examples include one or more suitably configured digital signal processors and other known electronic circuits, e.g. discrete logic gates interconnected to perform a specialized function, or Application Specific Integrated Circuits (ASICs).

Alternatively, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

The proposed technology thus provides an image reconstruction system configured to perform the method described herein.

In particular, there is provided an apparatus for image reconstruction based on image data from a photon-counting multi-bin x-ray detector. The apparatus is configured to determine parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum. The apparatus is further configured to perform image reconstruction based on the image data and the determined parameters.

Figure 11:
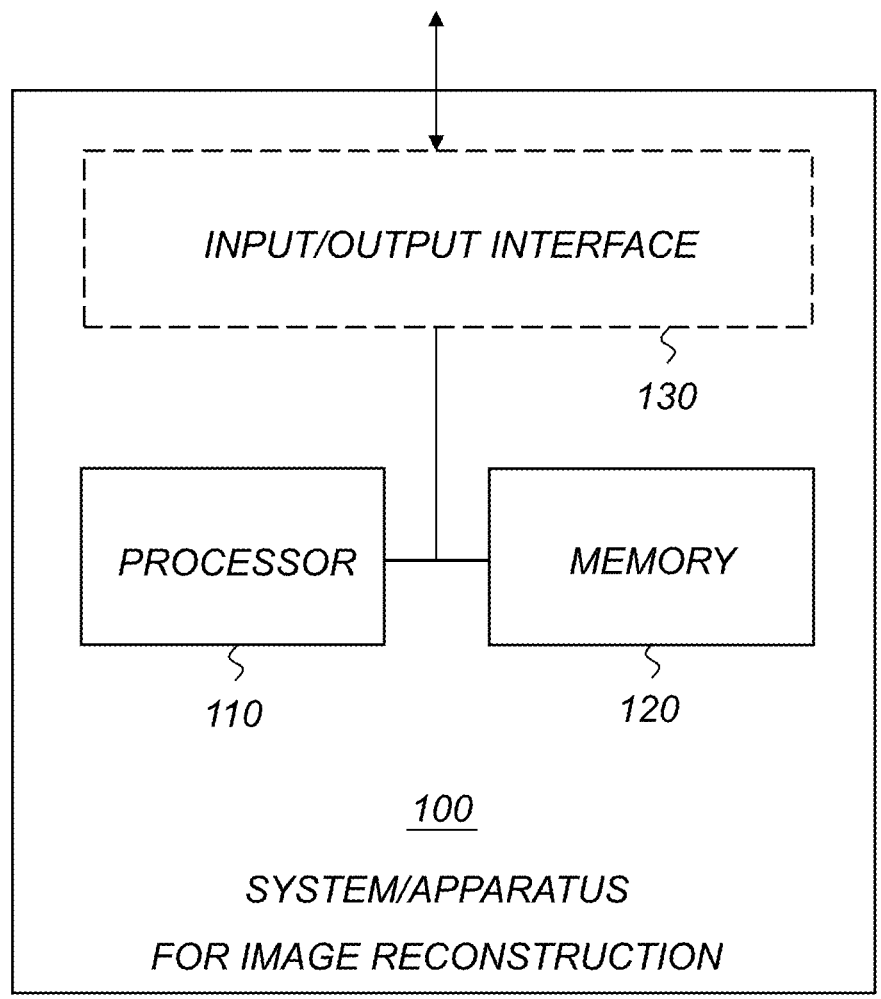
FIG. 11 is a schematic diagram illustrating an example of a system/apparatus for image reconstruction according to an embodiment.

In a particular example, the apparatus 100 comprises a processor 110 and a memory 120, the memory comprising instructions executable by the processor, whereby the processor is operative to determine the parameters and perform the image reconstruction, as illustrated in FIG. 11. Optionally, the apparatus comprises an input/output interface for receiving input data and outputting resulting output data.

In this particular example, at least some of the steps, functions, procedures, modules and/or blocks described herein are implemented in a computer program, which is loaded into the memory for execution by processing circuitry including one or more processors. The processor(s) and memory are interconnected to each other to enable normal software execution. An optional input/output device may also be interconnected to the processor(s) and/or the memory to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors is thus configured to perform, when executing the computer program, well-defined processing tasks such as those described herein.

The processing circuitry does not have to be dedicated to only execute the above-described steps, functions, procedure and/or blocks, but may also execute other tasks.

Figure 12:
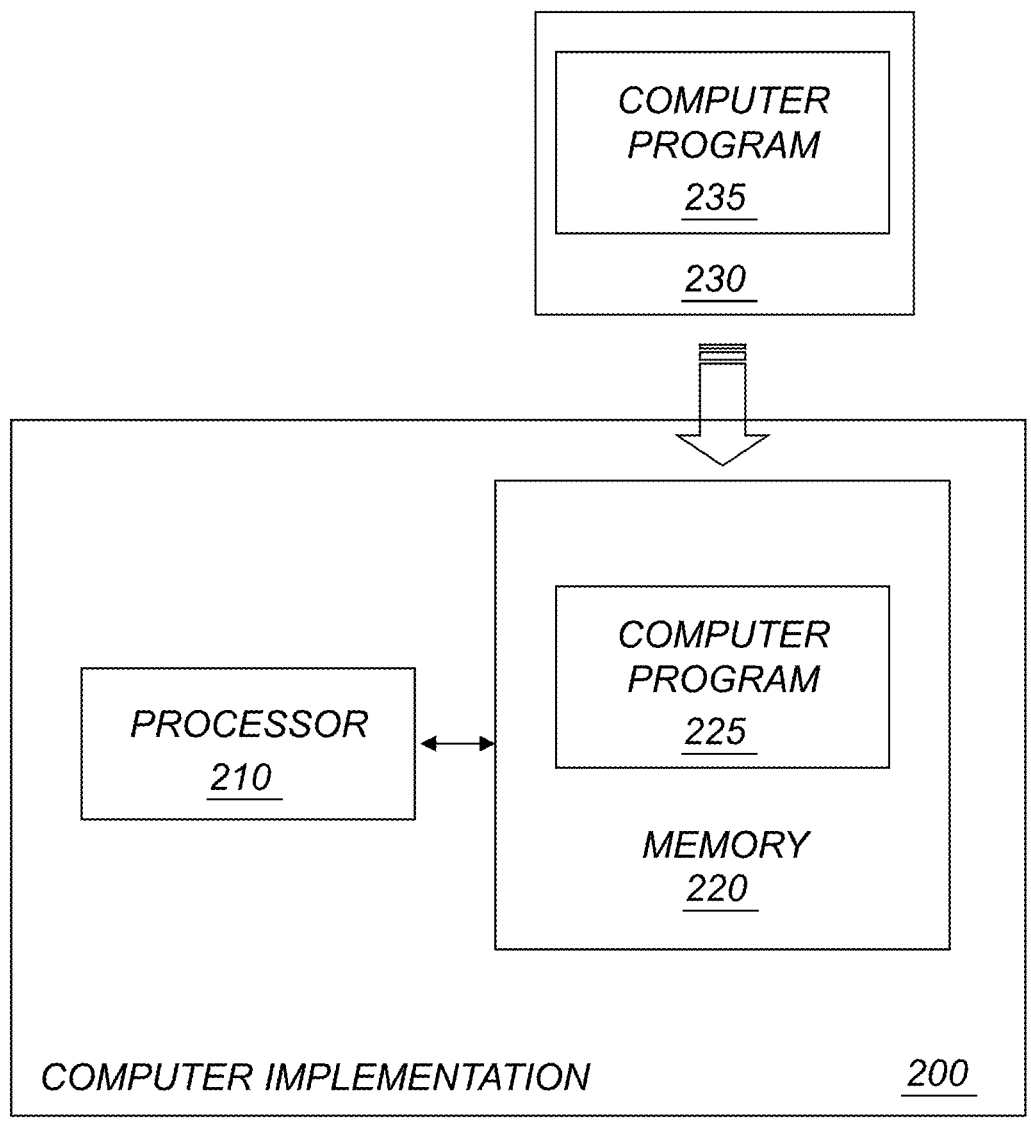
FIG. 12 is a schematic diagram illustrating an example of computer implementation according to an embodiment.

FIG. 12 is a schematic diagram illustrating another example of computer implementation according to an embodiment.

In a particular embodiment, there is provided a computer program 225; 235 for use with a photon-counting multi-bin x-ray detector. The computer program 225; 235 comprises instructions, which when executed by at least one processor 110; 210, cause the at least one processor to:
- determine parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum, and
- perform image reconstruction based on image data from the x-ray detector and the determined parameters.

The proposed technology also provides a computer-program product comprising a computer-readable medium 220; 230) having stored thereon such a computer program.

By way of example, the software or computer program 225; 235 may be realized as a computer program product, which is normally carried or stored on a computer-readable medium 220; 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program may thus be loaded into the operating memory of a computer or equivalent processing device for execution by the processing circuitry thereof.

Figure 13:
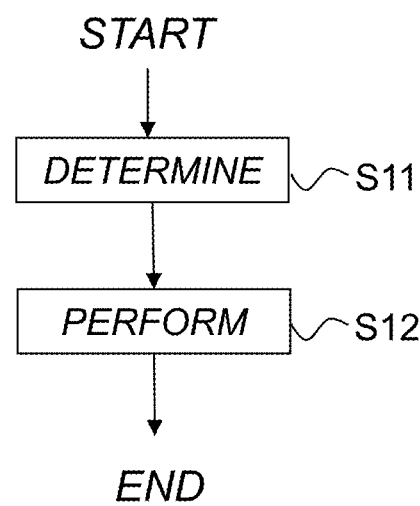
FIG. 13 is a schematic diagram illustrating an example of a computer flow diagram according to an embodiment.

The flow diagram or diagrams presented herein may be regarded as a computer flow diagram or diagrams, an example of which is illustrated in FIG. 13, when performed by one or more processors. A corresponding device, system and/or apparatus may be defined as a group of function modules, where each step performed by the processor corresponds to a function module. In this case, the function modules are implemented as a computer program running on the processor. Hence, the device, system and/or apparatus may alternatively be defined as a group of function modules, where the function modules are implemented as a computer program running on at least one processor.

The computer program residing in memory may thus be organized as appropriate function modules configured to perform, when executed by the processor, at least part of the steps and/or tasks described herein.

Figure 14:
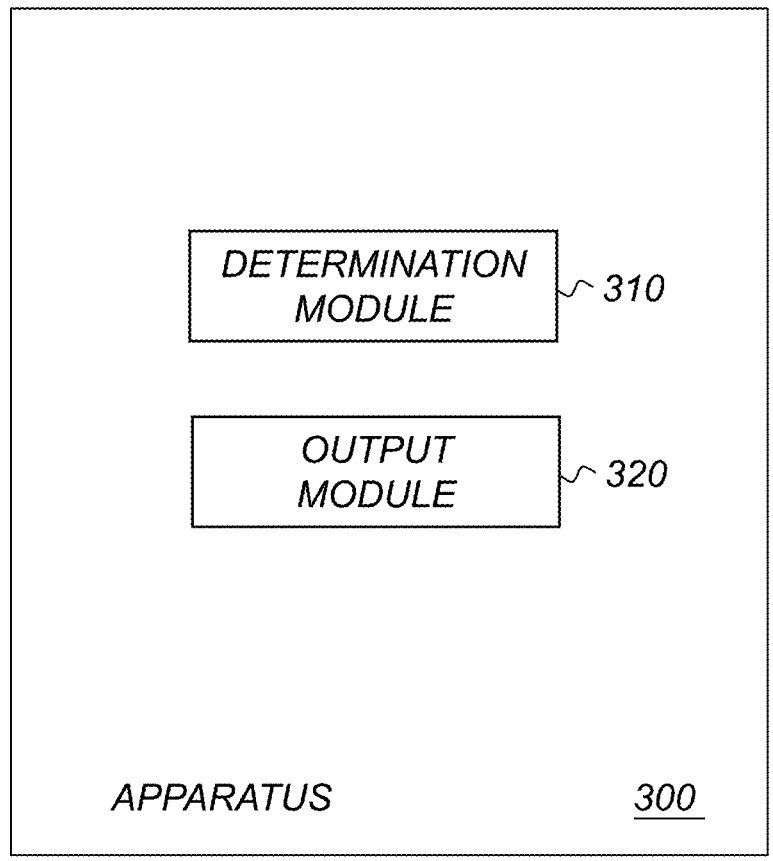
FIG. 14 is a schematic diagram illustrating an example of an apparatus for supporting image reconstruction.

FIG. 14 is a schematic diagram illustrating an example of an apparatus for supporting image reconstruction.

The apparatus 300 is adapted for supporting image reconstruction based on image data from a photon-counting x-ray detector. The apparatus 300 comprises a determination module 310 for determining parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum. The apparatus 300 also comprises an output module 320 for outputting the determined parameters to an image reconstruction system for enabling adjustments in the image reconstruction procedure based on the determined parameters.

Alternatively it is possibly to realize the modules in FIG. 14 predominantly by hardware modules, or alternatively by hardware. The extent of software versus hardware is purely implementation selection.

The embodiments described above are merely given as examples, and it should be understood that the proposed technology is not limited thereto. It will be understood by those skilled in the art that various modifications, combinations and changes may be made to the embodiments without departing from the present scope as defined by the appended claims. In particular, different part solutions in the different embodiments can be combined in other configurations, where technically possible.

REFERENCES

1. C. Xu et al. "Evaluation of a second-generation ultra-fast energy-resolved ASIC for photon-counting spectral CT" IEEE Transactions on Nuclear Science, vol. 60, no. 1, pp. 437-445, February 2013
2. M. Persson and H. Bornefalk, "A Framework for Evaluating Threshold Variation Compensation Methods in Photon Counting Spectral CT", IEEE Transactions on Medical Imaging, vol. 31, no. 10, pp. 1861-1874, October 2012
3. E. Roessl and R. Proksa, "K-edge imaging in x-ray computed tomography using multi-bin photon counting detectors", Phys. Med. Biol. 52 (2007) 4679-4696
4. X. Liu, H. Bornefalk, H. Chen, M. Danielsson, S. Karlsson, M. Persson, X. Cheng, and B. Huber, "A silicon-strip detector for photon-counting spectral CT: energy resolution from 40 keV to 120 keV," IEEE Transactions on Nuclear Science, 61(3):1099-1105, 2014
5. T. G. Schmidt, "An empirical method for correcting the detector spectral response in energy-resolved CT," in Medical Imaging 2012: Physics of Medical Imaging, Proc. SPIE 8313, 831312, SPIE 2012.
6. Seungwan Lee et al "Quantitative material decomposition using spectral computed tomography with an energy-resolved photon-counting detector" Phys. Med. Biol. 59 5457, 2014
7. J. Jakubek, "Data processing and image reconstruction methods for pixel detectors," Nucl. Instr. and Meth. A, vol. 576, no. 1, pp. 223-234, June 2007, proceedings of the 8th International Workshop on Radiation Imaging Detectors.
8. R. E. Alvarez, "Estimator for photon counting energy selective x-ray imaging with multi-bin pulse height analysis" Med. Phys. 38 (5), 2324-2334, 2011
9. H. Bornefalk, M. Persson and M. Danielsson, "Necessary forward model specification accuracy for basis material decomposition in spectral CT", Proc. of SPIE, Physics of Medical Imaging, San Diego February 2014, vol: 9033, pp. 903321-1-9
10. U.S. Pat. No. 7,756,239 B2
11. U.S. Pat. No. 8,422,636 B2
12. U.S. Pat. No. 7,983,397 B2

13. U.S. Pat. No. 8,000,434 B2
14. US 2014/0105369
15. JP 2011/085479
16. US 2013/0301798

The invention claimed is:

1. A method of image reconstruction based on image data from a photon-counting multi-bin x-ray detector, wherein said method comprises:
determining parameter(s) of a given functional form of the relationship between comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum;
performing image reconstruction based on the image data and the determined parameter(s).

2. The method of claim 1, wherein the determined parameter(s) is/are used for adjustments in the image reconstruction procedure.

3. The method of claim 1, wherein the reference pulse height spectrum is expressed in units of energy and the measured pulse height spectrum is expressed in units of voltage.

4. The method of claim 1, wherein the first set of data representative of a measured pulse height spectrum is based on a measured x-ray spectrum, and the second set of data representative of a reference pulse height spectrum is based on a previously acquired reference x-ray spectrum or a simulated x-ray spectrum.

5. The method of claim 4, wherein the fitting procedure is performed between a measured accumulated x-ray spectrum and a simulated accumulated x-ray spectrum, taking physical detector characteristics into consideration in the simulation.

6. The method of claim 4, wherein the fitting procedure is performed between a measured accumulated x-ray spectrum and a previously acquired accumulated x-ray spectrum.

7. The method of claim 4, wherein the first set of data representative of a measured pulse height spectrum corresponds to a differentiated version of a measured accumulated x-ray spectrum, and the second set of data representative of a reference pulse height spectrum corresponds to a differentiated version of an accumulated reference x-ray spectrum.

8. The method of claim 7, wherein a measured accumulated x-ray spectrum, and a corresponding accumulated reference x-ray spectrum are differentiated, and the fitting procedure is performed between the differentiated measured accumulated x-ray spectrum and the differentiated reference accumulated x-ray spectrum.

9. The method of claim 8, wherein the number of measurement points and their setting in voltage are chosen so that the corresponding differentiated x-ray spectrum is a histogram of counts in each detection bin, and the parameter(s) is/are determined based on histogram data for each of a number of channels in the read-out chain of the x-ray detector and corresponding reference histogram data.

10. The method of claim 1, wherein a broad x-ray spectrum of an x-ray source associated with the imaging modality is used to acquire an accumulated spectrum of counts as a function of comparator voltage, and the first set of data representative of a measured pulse height spectrum is based on the acquired accumulated spectrum of counts.

11. The method of claim 1, wherein the parameter(s) include an array $p_i$ of one or more parameters relating the voltage $U_i$ of the measured pulse height spectrum with the energy $E_i$ of the reference pulse height spectrum according to $U_i = f(E_i; p_i)$, where f is a given function and the subscript i denotes the read-out channel.

12. The method of claim 1, wherein the parameters include gain $g_i$ and offset $m_i$ relating the voltage $U_i$ of the measured pulse height spectrum with the energy $E_i$ of the reference pulse height spectrum according to $U_i = g_i E_i + m_i$, where the subscript i denotes the read-out channel.

13. The method of claim 1, wherein the fitting procedure is performed for each of a number of channels in the read-out chain of the x-ray detector.

14. An apparatus configured to perform image reconstruction based on image data from a photon-counting multi-bin x-ray detector,
wherein said apparatus is configured to determine parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum, and
wherein said apparatus is configured to perform image reconstruction based on the image data and the determined parameters.

15. The apparatus of claim 14, wherein said apparatus comprises a processor and a memory, said memory comprising instructions executable by the processor, whereby the processor is operative to determine the parameters and perform the image reconstruction.

16. A computer-program product comprising a computer-readable medium having stored thereon a computer program for use with a photon-counting multi-bin x-ray detector, said computer program comprising instructions, which when executed by at least one processor, cause the at least one processor to:
determine parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum, and
perform image reconstruction based on image data from the x-ray detector and the determined parameters.

17. An apparatus for supporting image reconstruction based on image data from a photon-counting x-ray detector, wherein said apparatus comprises:
a determination module for determining parameters of a given functional form of the relationship between assigned comparator settings expressed in voltage in the read-out chain of the x-ray detector and the corresponding energy threshold values expressed in energy based on a fitting procedure between a first set of data representative of a measured pulse height spectrum and a second set of data representative of a reference pulse height spectrum, and
an output module for outputting the determined parameters to an image reconstruction system for enabling adjustments in the image reconstruction procedure based on the determined parameters.

* * * * *